US00PP15524P2

(12) United States Plant Patent
Bessho et al.

(10) Patent No.: US PP15,524 P2
(45) Date of Patent: Feb. 1, 2005

(54) ***CALIBRACHOA* PLANT NAMED 'KAKEGAWA S69'**

(50) Latin Name: ***Calibrachoa* species**
Varietal Denomination: Kakegawa S69

(75) Inventors: Masao Bessho, Kakegawa (JP); Toshimi Ohga, Kikugawa (JP)

(73) Assignee: Sakata Seed Corporation, Yokohama (JP)

( * ) Notice: Subject to any disclaimer, the term of this patent is extended or adjusted under 35 U.S.C. 154(b) by 5 days.

(21) Appl. No.: 10/802,075

(22) Filed: Mar. 15, 2004

(51) Int. Cl.[7] ..... A01H 5/00
(52) U.S. Cl. ..... Plt./263
(58) Field of Search ..... Plt./263, 356

*Primary Examiner*—Kent Bell
(74) *Attorney, Agent, or Firm*—Jondle & Associates P.C.

(57) ABSTRACT

'Kakegawa S69' is a new variety of *Calibrachoa* plant. This new variety has light red petal lobes with darker red corolla throat and petal mid-veins and yellow corolla tube and dark green foliage.

1 Drawing Sheet

Genus/species: *Calibrachoa* species.
Varietal denomination: 'Kakegawa S69'.

BACKGROUND OF THE INVENTION

'Kakegawa S69' originated from a hybridization made in November 1999 in Kakegawa, Japan. The female parent was a *Calibrachoa* breeding line with scarlet colored flowers and semi-creeping habit known as 9B-74A. The male parent was a *Calibrachoa* breeding line with pale apricot colored flowers and mounding habit known as 9B-22B.

In February 2000, $F_1$ seed was sown from this cross and plants were transplanted to outdoors. These plants ranged from erect to semi-creeping habit and light orange to apricot flower color. Four plants with semi-creeping habit, light orange petals and pale corolla tube were selected and vegetatively propagated. In August 2000, these selections were evaluated again in an open field as plants generated from vegetative cuttings. One plant line was selected for its unique light orange flower color. The selection was vegetatively propagated again in February 2001 and evaluated in 9 cm hanging pots in a greenhouse and in an open field.

The selection was further evaluated from new vegetative plants in Salinas, Calif. during 2002. The selection was subsequently named 'Kakegawa S69'. 'Kakegawa S69' was asexually reproduced by stem cuttings in Salinas, Calif. and was determined to have its characteristics firmly fixed in successive generations of asexual propagation.

DESCRIPTION OF PHOTOGRAPH

This new *Calibrachoa* plant is illustrated by the accompanying photograph which shows blooms and foliage of the plant in full color. The colors shown being as true as can be reasonably obtained by conventional photographic procedures.

DESCRIPTION OF THE GENUS *CALIBRACHOA* LLAVE & LEX

Figure 1:
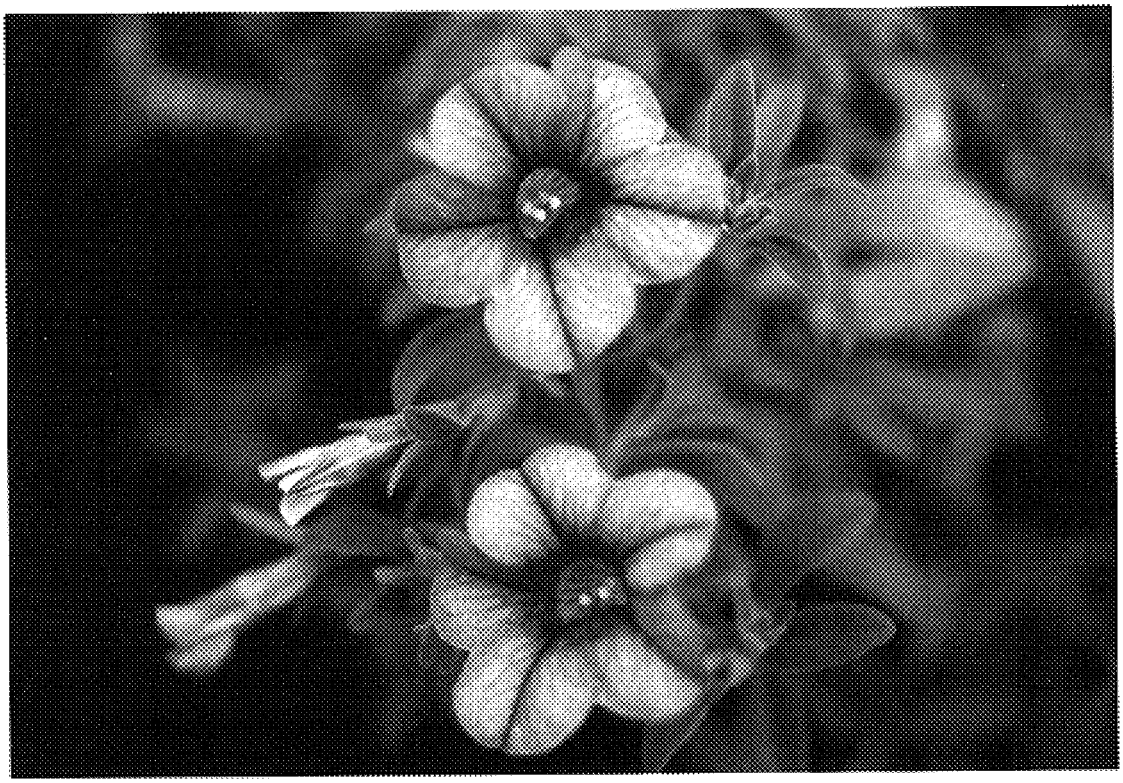
FIG. 1 shows a close-up view of flowers.
Figure 2:
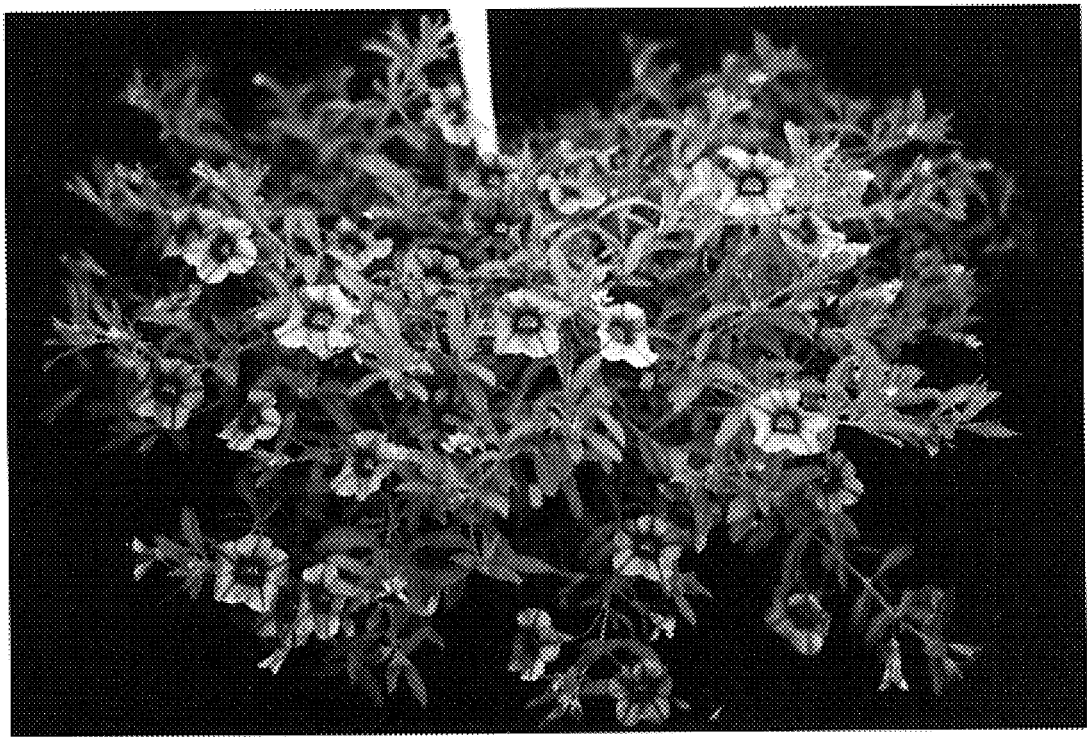
FIG. 2 shows the entire plant.

The genus *Petunia* was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden *Petunia,* and the inter-relationship of several species classified as *Petunia.* These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne*. Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990, Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently, a proper description has not been written for *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, a single outermost petal covers the other four, radially folded and terminally contorted petals. *Calibrachoa* flower buds are flat with all five petals linearly folded and the two lower petals forming a cover around the three other petals and fused together.

ENVIRONMENTAL CONDITIONS FOR PLANT GROWTH

The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 DIP 'N GROW:9 water) root-inducing solution immediately prior to sticking into the cells trays. Cuttings were stuck into plastic cell trays having 98 cells and containing a moistened peat moss-based growing medium. The cuttings were misted with water from overhead for 10 seconds every 30 minutes until sufficient roots were formed.

Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

DETAILED DESCRIPTION OF THE NEW PLANT

Data below collected on plants three months from rooted cutting. Five plants grown in 20 cm diameter pots were transplanted to a 41 cm hanging basket. Color references are to The R.H.S. Colour of The Royal Horticultural Society of London (R.H.S.). The following traits and characteristics describe the new variety.

Classification:
- *Family.*—Solanaceae.
- *Species.*—*Calibrachoa* sp.
- *Common names.*—*Calibrachoa.*

Parentage:
- *Female parent.*—Breeding line 9B-74A.
- *Male parent.*—Breeding line 9B-22B.

Growth:
- *Habit.*—Decumbent.
- *Height.*—23.0 cm.
- *Spread.*—115.0 cm when grown in a 41 cm hanging basket or pot, and using five 20 cm potted plants in the hanging basket.
- *Life cycle.*—Perennial.
- *Form.*—Branching.
- *Time to produce a rooted cutting.*—6 weeks.
- *Time to bloom from propagation.*—10 weeks.
- *Flowering requirements.*—Will flower so long as day length is greater than 12 hours and temperatures exceed 13° C.
- *Resistance/susceptibility.*—Excellent resistance to rain, heat and drought. Will not tolerate temperatures below 10° C. Plants are susceptible to Botrytis, powdery mildew, various stem and root rots and certain viruses, like Tobacco Mosaic Virus and Impatiens Necrotic Spotted Virus. Plants can be infested with aphids, leafminer, whitefly and various Lepidoptera.

Stems:
- *Stem color.*—RHS 144B (yellow-green).
- *Anthocyanin color.*—RHS N77A (purple).
- *Pubescence.*—Heavy.
- *Pubescence color.*—RHS N155A (white).
- *Stem description.*—Round.
- *Stem length.*—4.0 cm–5.0 cm.
- *Stem diameter.*—2.0 mm.
- *Internode length.*—1.5–2.5 cm.

Leaves:
- *Leaf arrangement.*—Alternate.
- *Leaf shape.*—Elliptical.
- *Leaf tip.*—Mucronate.
- *Leaf base.*—Decurrent.
- *Leaf margin.*—Entire.
- *Leaf surface.*—Rough, dull.
- *Leaf length.*—3.0 cm.
- *Leaf width.*—0.5 cm.
- *Leaf color.*—Upper surface: RHS 137A (green); lower surface: RHS 139B (green).
- *Leaf surface pubescence.*—Slight.
- *Leaf surface pubescence color.*—RHS 155B (white).
- *Petiole length.*—2.0 mm.
- *Petiole color.*—RHS 138B (green).
- *Venation.*—Pinnate.

Flowers:
- *Inflorescence type.*—Solitary.
- *Flowering habit.*—Indeterminate.
- *Duration of flower life.*—5 days.
- *Shape.*—The flowers are funnel shaped with five fissures and a shallow, yet prominent, indentation of the petal tip at the mid-vein.
- *Flower depth.*—2.0 cm–2.5 cm.
- *Floral tube length.*—1.3 cm–1.5 cm.
- *Floral tube diameter.*—0.6 cm–0.9 cm.
- *Flower diameter.*—2.5 cm.
- *Calyx.*—5 sepals, free; 1.8 cm×4 mm (L×W).
- *Sepal shape.*—Lanceolate.
- *Sepal apex.*—Mucronate.
- *Sepal margin.*—Entire.
- *Sepal color.*—RHS 143A (green).
- *Bud shape.*—Ovate.
- *Bud length.*—1.5 cm–2.0 cm.
- *Bud diameter.*—0.4 cm–0.5 cm.
- *Bud surface.*—Pubescent.
- *Bud color.*—RHS 149C (yellow-green).
- *Peduncle length.*—2.5 cm.
- *Peduncle color.*—RHS 144B (yellow-green).
- *Ovary.*—Superior.
- *Pistil number.*—1.
- *Stigma color.*—RHS 150C (yellow).
- *Style color.*—RHS 149B (yellow-green).
- *Corolla.*—5 petals, fused.
- *Petal shape.*—Spatulate.
- *Petal apex.*—Truncate.
- *Petal margin.*—Entire.
- *Petal pubescence.*—Glabrous.
- *Petal size.*—1.5 cm×2.0 cm.
- *Petal color.*—Lobes upper: RHS 40C (red) with RHS 46A (red) petal mid-veins and RHS N187B (greyed-purple) corolla throat; lower RHS 31D (orange-red) with RHS N186B (greyed-purple) mid-veins; Corolla tube: inner RHS 5C (yellow) with RHS N187B (greyed-purple) veins; outer RHS 10C (yellow) with RHS N186B (greyed-purple) veins.

*Stamen number.*—5, free.
*Stamen color.*—RHS 150C (yellow-green).
*Pollen color.*—RHS 8B (yellow).
*Fragrance.*—Absent.
*Seed production.*—None.

COMPARISON WITH MOST SIMILAR VARIETY

'Kakegawa S69' is a distinct variety of *Calibrachoa* owing to its light red petal lobes with darker red corolla throat and petal mid-veins and yellow corolla tube. 'Kakegawa S69' is most similar to the variety 'Kakegawa S52' (U.S. Plant Pat. No. 15,046); however, there are differences as shown in Table 1 below.

TABLE 1

| | 'Kakegawa S69' | 'Kakegawa S52' |
|---|---|---|
| Upper Petal Color | RHS 40C (red) with RHS 46A (red) petal mid-veins and RHS N187B (greyed-purple) corolla throat. | RHS 48C (red) with RHS 47A (red) corolla throat and petal mid-veins. |

What is claimed is:

1. A new and distinct cultivar of *Calibrachoa* plant as shown and described herein.

* * * * *